Figure 1:
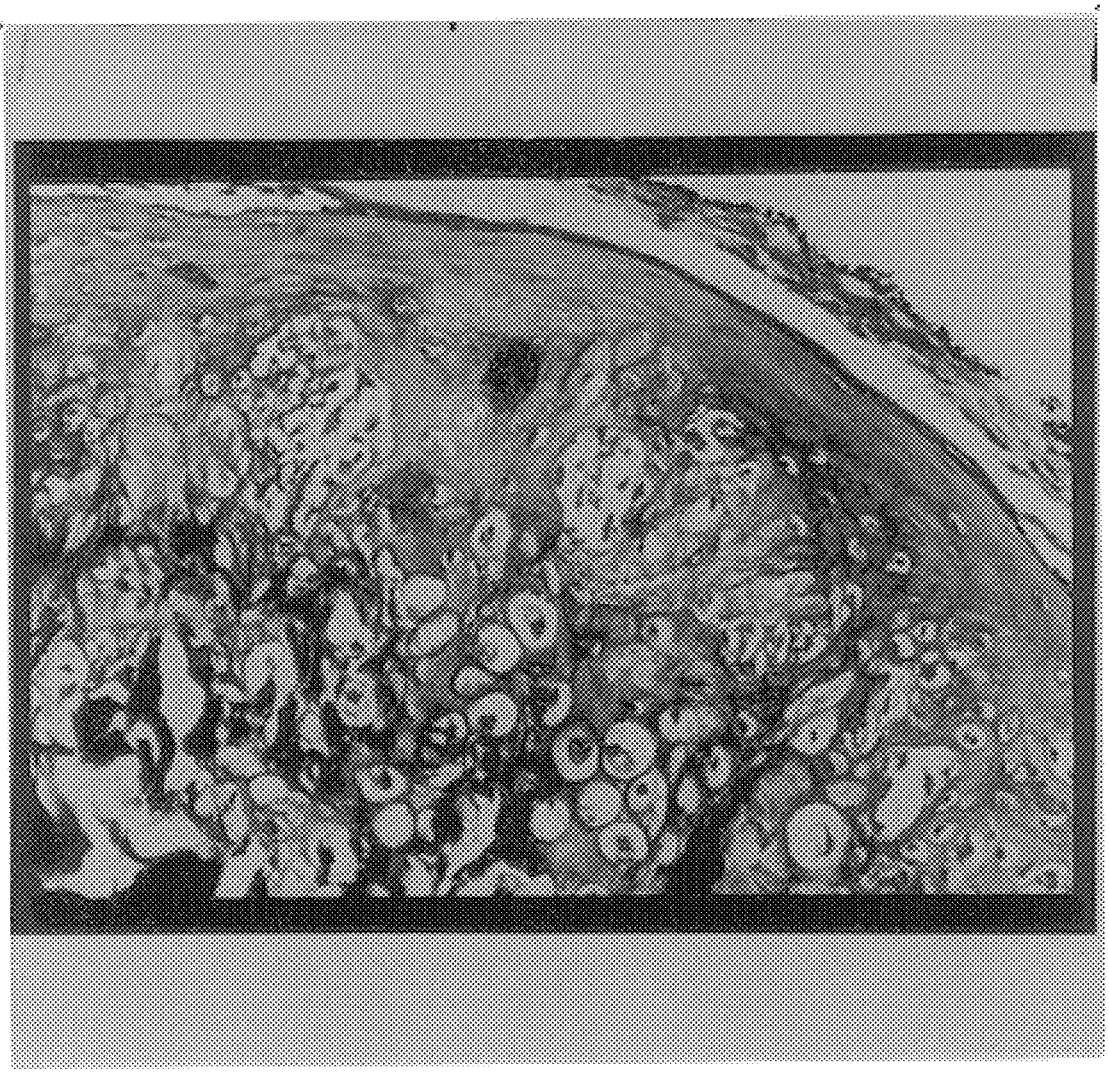

United States Patent [19]
Johnstone et al.

[11] Patent Number: 5,908,784
[45] Date of Patent: Jun. 1, 1999

[54] IN VITRO CHONDROGENIC INDUCTION OF HUMAN MESENCHYMAL STEM CELLS

[75] Inventors: Brian Johnstone; Jung Yoo, both of Shaker Heights, Ohio

[73] Assignee: Case Western Reserve University, Cleveland, Ohio

[21] Appl. No.: 08/749,484

[22] Filed: Nov. 15, 1996

Related U.S. Application Data

[60] Provisional application No. 60/006,866, Nov. 16, 1995.
[51] Int. Cl.$^6$ .............................. C12N 5/08; C12N 5/02; C12N 5/06; A61K 38/17
[52] U.S. Cl. .................... 435/372; 435/377; 435/395; 435/397; 435/405; 530/356
[58] Field of Search .................... 435/395, 397, 435/405, 372, 377; 530/356

[56] References Cited

U.S. PATENT DOCUMENTS

| | | |
|---|---|---|
| 5,197,985 | 3/1993 | Caplan et al. . |
| 5,226,914 | 7/1993 | Caplan et al. . |
| 5,436,151 | 7/1995 | McGlave et al. . |
| 5,466,572 | 11/1995 | Sasaki et al. . |
| 5,486,359 | 1/1996 | Caplan . |
| 5,646,001 | 7/1997 | Terstappen et al. . |

OTHER PUBLICATIONS

Ager et al., (eds.), *Imm. Today: Immune Receptor Supplement* 2nd ed.:1–36 (1997).
Ashton et al., *Clin Orthop Rel Res*. 151:294–307 (1980).
Avraham et al., *Blood*, 83(8):2126–2132 (1994).
Ballock et al., *J. Cell Biol*, 126(5):1311–1318 (1994).
Beresford, *Clin Orthop Rel Res*, 240:270–280 (1989).
Bruder et al., *Bone and Mineral*, 11:141–151 (1990).
Caplan, *Levels of Genetic Control in Development*, 37–68 (1981).
Dennis et al., *Cell Transpl*, 1:23–32 (1992).
Ellis et al., *Blood Reviews*, 9(1):1–6 (1995).
Elmer et al., *Teratology*, 24:215–223 (1981).
Goshima et al., *Clin Orthop Rel Res*, 269:274–283 (1991).
Hauschka, *Developmental Biology*, 37(2):345–368 (1974).
Kato, et al., *Proc. Natl. Acad. Sci. USA*, 85:9552–9556 (1988).
Koller et al., *Stem Cells*, 15(4):305–313 (1997).
Nakahara et al., *Experimental Cell Research*, 195:492–503 (1991).
Solursh et al., *Developmental Biology*, 83(1)9–19 (1981).
Solursh et al., *Journal of Cellular Biochemistry*, 45:258–260 (1991).
Swalla et al., *Developmental Biology*, 116:31–38 (1986).
Lennon, DP et al. Experimental Cell Research. 219(1):211–222, Jul. 1995.
Grigoriadis, AE et al. J. Cell Biol. 106:2139–2155, Jun. 1988.
Hirano, H et al. Clin. Orth. Rel. Res. 154:234–248, Jan. 1981.
Wang, EA et al. Growth Factors. 9:57–71, Jul. 1993.
Bortell, R et al. J. Cell. Biochem. 54(2):256–263, Feb. 1994.
Crnek, V et al. Int. J. Devel. Biol. 35(3):197–202, Sep. 1991.

*Primary Examiner*—David Saunders
*Assistant Examiner*—F. Pierre Vander Vegt
*Attorney, Agent, or Firm*—Elliot M. Olstein; Raina Semionow

[57] ABSTRACT

Disclosed are a composition of chemically defined components which support the in vitro chondrogenesis of mesenchymal progenitor cells, a method for in vitro chondrogenic induction of such progenitor cells and a method of forming human chondrocytes in vitro from such progenitor cells.

28 Claims, 5 Drawing Sheets

IN VITRO CHONDROGENIC INDUCTION OF HUMAN MESENCHYMAL STEM CELLS

This application claims priority of provisional application Ser. No. 60/006,866 filed Nov. 16, 1995.

The present invention relates to the field of methods and compositions for directing mesenchymal progenitor cells cultivated in vitro to differentiate into specific cell lineage pathways, and particularly to such directed lineage induction prior to, or at the time of, their implantation into a recipient or host for the therapeutic treatment of pathologic conditions in humans and other species.

Mesenchymal stem cells (MSCs) are the formative pluripotent blast or embryonic-like cells found in bone marrow, blood, dermis, and periosteum that are capable of differentiating into specific types of mesenchymal or connective tissues including adipose, osseous, cartilaginous, elastic, muscular, and fibrous connective tissues. The specific differentiation pathway which these cells enter depends upon various influences from mechanical influences and/or endogenous bioactive factors, such as growth factors, cytokines, and/or local microenvironmental conditions established by host tissues. Although these cells are normally present at very low frequencies in bone marrow, a process for isolating, purifying, and mitotically expanding the population of these cells in tissue culture is reported in Caplan et al. U.S. Pat. Nos. 5,197,985 and 5,226,914.

In prenatal organisms, the differentiation of MSCs into specialized connective tissue cells is well established; for example embryonic chick, mouse or human limb bud mesenchymal cells differentiate into cartilage, bone and other connective tissues (Caplan A I, In: *39th Annual Symposium of the Society for Developmental Biology*, ed by S. Subtelney and U Abbott, pp 3768. New York, Alan R Liss Inc, 1981; Elmer et al., *Teratology*, 24:215–223, 1981; Hauschka S D, DevBiol, 37:345–368, 1974; Solursh et al., *Dev Biol*, 83:9–19, 1981; Swalla et al., *Dev Biol*, 116:31–38, 1986). In addition, a clonal rat fetus calvarial cell line has also been shown to differentiate into muscle, fat, cartilage, and bone (Goshima et al., *Clin Orthop Rel Res*, 269:274–283, 1991). The existence of MSCs in post-natal organisms has not been widely studied with the objective of showing the differentiation of post-embryonic cells into several mesodermal phenotypes. The few studies which have been done involve the formation of bone and cartilage by bone marrow cells following their encasement in diffusion chambers and in vivo transplantation (Ashton et al., *Clin Orthop Rel Res*, 151:294–307, 1980; Bruder et al., *Bone Mineral*, 11:141–151, 1990). Recently, cells from chick periosteum have been isolated, expanded in culture, and, under high density conditions in vitro, shown to differentiate into cartilage and bone (Nakahara et al., *Exp Cell Res*, 195:492–503, 1991). Rat bone marrow-derived mesenchymal cells have been shown to have the capacity to differentiate into osteoblasts and chondrocytes when implanted in vivo (Dennis et al., *Cell Transpl*, 1:2332, 1991; Goshima et al., *Clin Orthop Rel Res*, 269:274–283, 1991). Although indirect evidence of their chondrogenic ability has been gained from implantation studies, no in vitro system has been developed in which these cells differentiate into chondrocytes.

In accordance with the present invention it has been observed by the inventors that when human mesenchymal stem cells are associated in a three-dimensional format they can be induced to commit and differentiate along the chondrogenic pathway when contacted in vitro with certain chondroinductive agents or factors. The three dimensional format is critical to the in vitro chondrogenesis of the invention and the cells are preferably condensed together, for example, as a packed or pelleted cell mass. This in vitro process is believed to recapitulate that which occurs in vivo and can be used to define the molecular events that are important in the process of chondrogenesis.

Thus, in one aspect the invention provides a composition for the in vitro chondrogenesis of human mesenchymal precursor cells and the in vitro formation of human chondrocytes therefrom, which composition comprises isolated human mesenchymal stem cells in a three dimensional format and at least one chondroinductive agent in contact therewith. The mesenchymal stem cells are preferably isolated, culture expanded human mesenchymal stem cells in a chemically defined serum-free environment and are condensed into close proximity, such as in the form of a three dimensional cell mass, e.g. packed cells or a centrifugal cell pellet.

The chondroinductive agent is preferably selected, individually or in combination, from the group consisting of (i) a glucocorticoid such as dexamethasone; (ii) a member of the transforming growth factor-β superfamily such as a bone morphogenic protein (preferably BMP-2 or BMP-4), TGF-β1, inhibin A or chondrogenic stimulating activity factor; (iii) a component of the collagenous extracellular matrix such as collagen I (particularly in the form of a gel); and (iv) a vitamin A analog such as retinoic acid. Particularly preferred is the combination of dexamethasone and TGF-β1.

The invention also provides a process for producing chondrocytes from mesenchymal stem cells by contacting mesenchymal stem cells with a chondroinductive agent in vitro where the stem cells are associated in a three dimensional format.

The invention also provides a process for inducing chondrogenesis in mesenchymal stem cells by contacting mesenchymal stem cells with a chondroinductive agent in vitro where the stem cells are associated in a three dimensional format.

In the above methods, the mesenchymal stem cells are preferably isolated, culture expanded human mesenchymal stem cells in a chemically defined serum-free environment and are condensed into close proximity, such as in the form of a three dimensional cell mass, e.g. packed cells or a centrifugal cell pellet. Further, the contacting preferably comprises culturing a pellet of human mesenchymal precursor cells in a chemically defined serum-free medium which comprises (1) a chemically defined minimum essential medium; (2) ascorbate or an analog thereof; (3) an iron source; (4) insulin or an insulin-like growth factor; and (5) at least one chondroinductive agent or factor. The above methods can also preferably comprise steps where the cells are cultured with the chondroinductive composition and thereafter placed in a rigid porous vessel, such as a ceramic cube.

It is also possible to use an isolated, non-cultured non-homogeneous human mesenchymal stem cell preparation in the composition and methods of the invention. MSCs can be isolated as non-cultured, non-homogeneous preparations, such as by density gradient fractionation, from tissue such as bone marrow, blood (including peripheral blood), periosteum and dermis, and other tissues which have mesodermal origins. In this regard, it has been found that although these mesenchymal stem cells are normally present in bone marrow, for example, in very minute amounts and that these amounts greatly decrease with age (i.e. from about $1/10,000$ cells in a relatively young patient to as few as $1/2,000,000$ in an elderly patient), human mesenchymal stem cell preparations can be isolated from tissue, particularly bone marrow, so as to be substantially free of other types of cells in the marrow. It is contemplated that the isolated fractionation preparation will comprise cells of which at least about 90%, and preferably at least about 95%, are human mesenchymal stem cells.

The sequence of events that occur in the induction of chondrogenesis and production of chondrocytes in the above in vitro methods resembles that of chondrogenesis in embryonic limb formation. Since all components of the system are defined, the system can be used as a valuable research tool for studies of the effects of growth factors etc. on the progression of chondrogenesis. It is also applicable to studies of the molecular control of mammalian chondrogenesis from progenitor cells.

The invention will now be further described by reference to a brief description of each of the Figures, which are in no way are a limitation of the scope of the invention.

FIG. 1. Toluidine blue staining of a section through a mesenchymal progenitor cell-laden collagen sponge harvested three weeks after subcutaneous implantation into a nude mouse. Rabbit bone marrow derived cells were grown for fourteen days in monolayer culture prior to loading into the sponge.

Figure 2A:
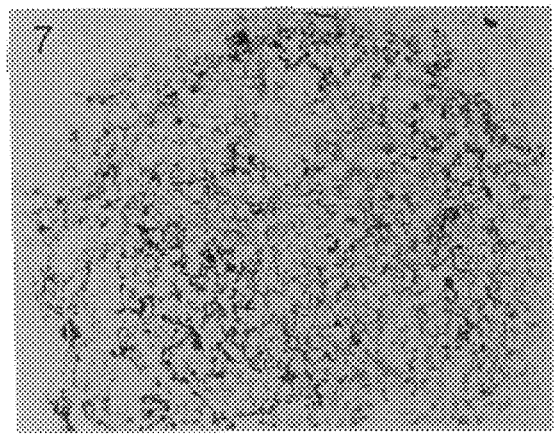
Figure 2B:
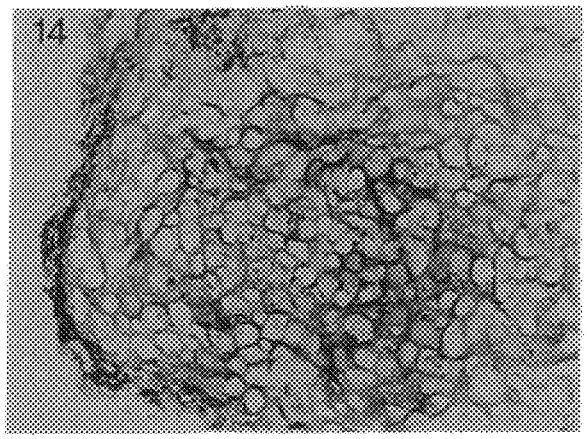
Figure 2C:
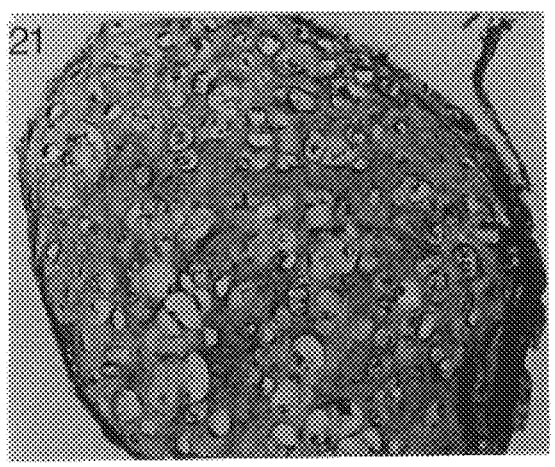

FIGS. 2A–2C. Toluidine blue staining of sections of pelleted rabbit bone marrow-derived mesenchymal progenitor cells from +DEX cultures at 7 (FIG. 2A), 14 (FIG. 2B) and 21 (FIG. 2C) days.

Figure 3A:
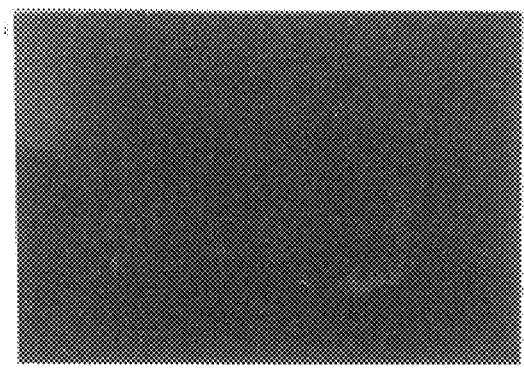
Figure 3B:
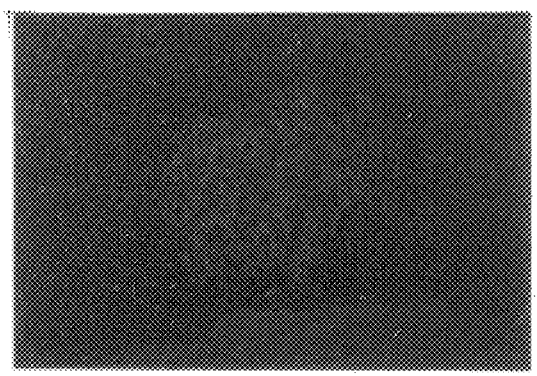
Figure 3C:
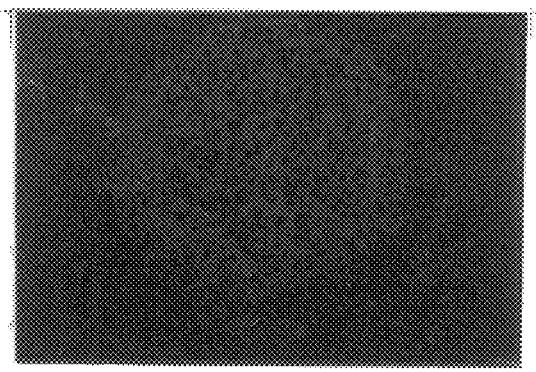
Figure 3D:
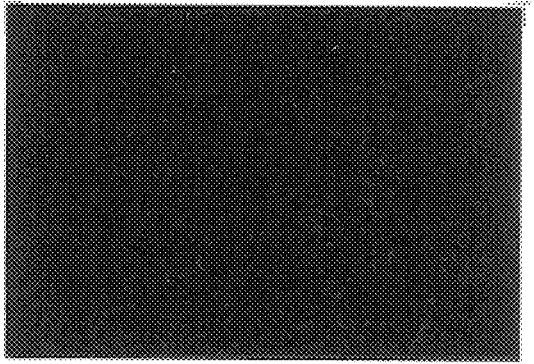
Figure 3E:
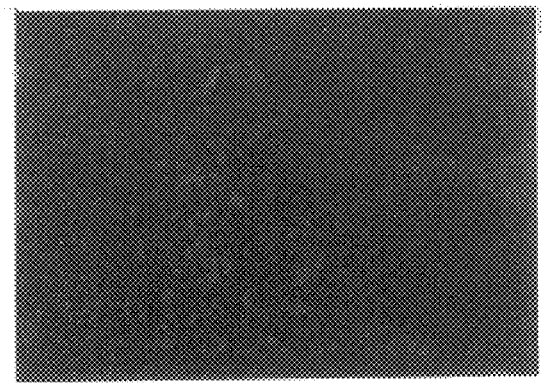
Figure 3F:
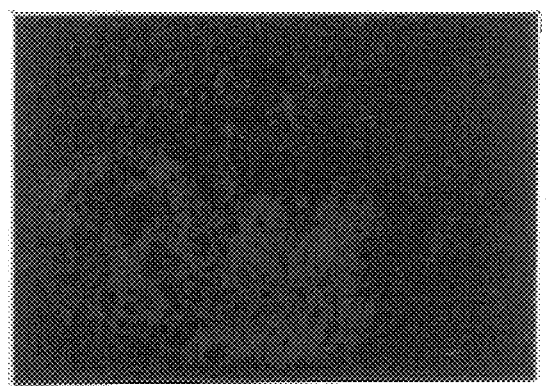
Figure 3G:
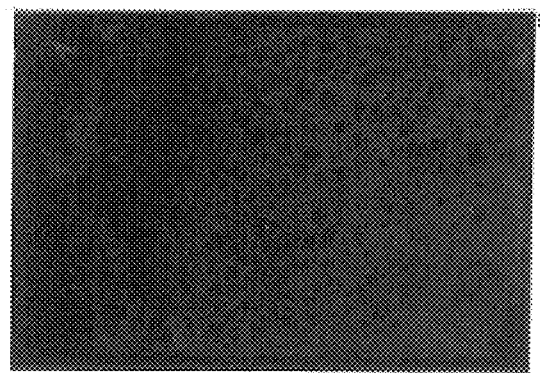

FIGS. 3A–3G. Immunohistochemistry of pellet-cultured rabbit bone marrow-derived mesenchymal progenitor cells. Immunostaining for type II collagen at days 7(FIG. 3A), 14(FIG. 3B) and 21(FIG. 3C). FIG. 3D is a section of a day 21 pellet immunostained for type X collagen. Immunostaining is also shown for glycosaminoglycans: chondroitin sulfate (7-D-4 in FIG. 3E; 3-B-3(+) in FIG. 3F) and keratan sulfate (5-D-4 in FIG. 3G).

Figure 4:
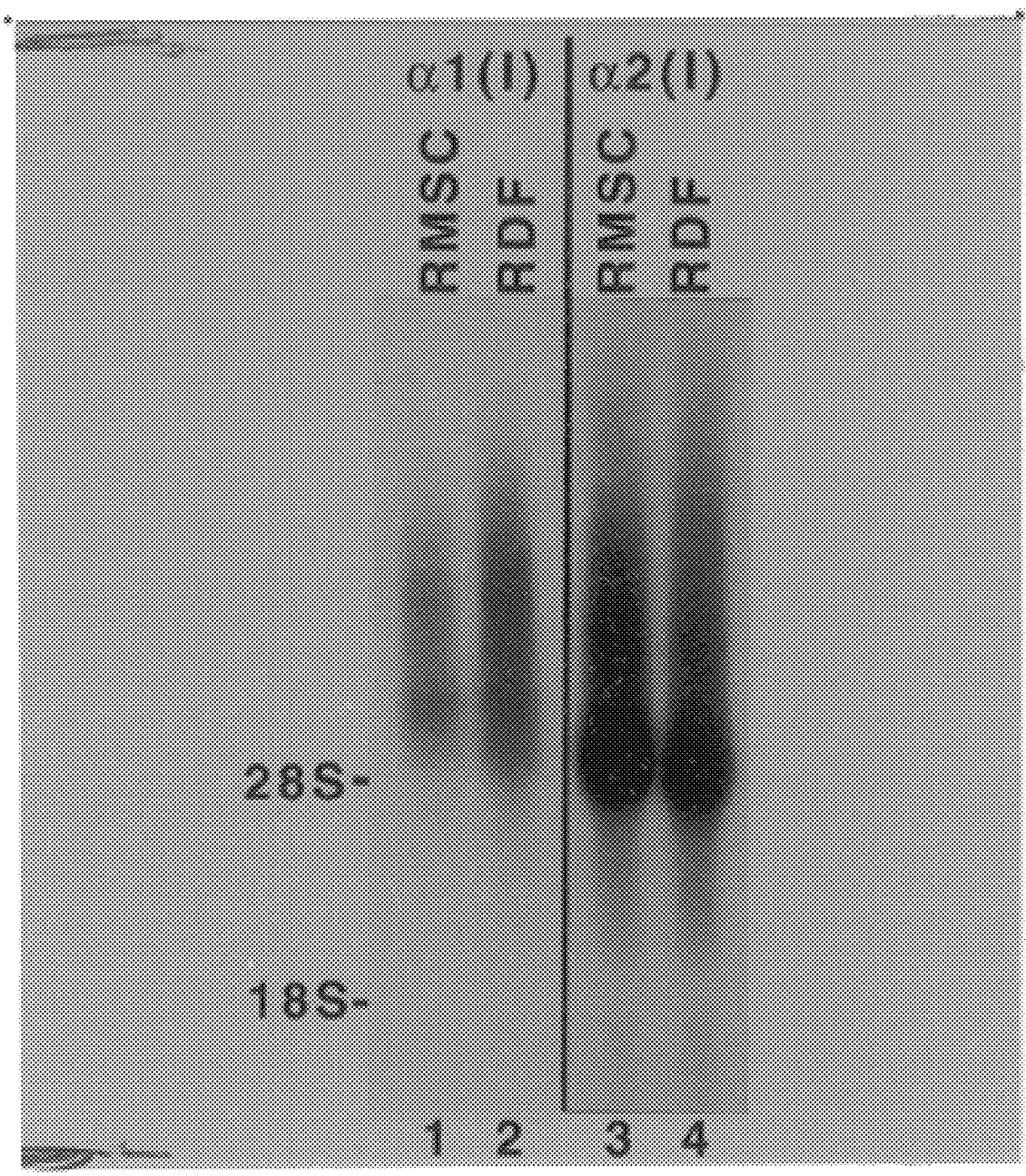

FIG. 4. Northern hybridization of rabbit mesenchymal progenitor cell RNA with matrix molecule probes. Total cellular RNA from rabbit bone marrow-derived mesenchymal progenitor cells (lanes 1,3) and rabbit dermal fibroblasts (lanes 2,4) was hybridized with a human collagen α1(I) probe (lanes 1,2) and a rabbit-specific probe for collagen α2(I) (lanes 3,4). No mRNA bands were detectible when the same blots were re-probed with human α1(II) and rabbit-specific aggrecan and link protein probes.

The invention will now be described in more detail with respect to numerous embodiments and examples in support thereof.

This invention has multiple uses and advantages. One such advantage lies in the ability to direct and accelerate MSC differentiation prior to implantation back into autologous hosts. For example, MSCs which are directed in vitro to become chondrogenic cells will synthesize cartilage matrix at an implant site more rapidly and uniformly than MSCs which must first be recruited into the lineage and then progress through the key differentiation steps. Such an ex vivo treatment also provides for uniform and controlled application of bioactive factors to purified MSCs, leading to uniform lineage commitment and differentiation. In vivo availability of endogenous bioactive factors cannot be as readily assured or controlled. A pretreatment step such as is disclosed herein circumvents this. In addition, by pretreating the MSCs prior to implantation, potentially harmful side effects associated with systemic or local administration of exogenous bioactive factors are avoided. Another use of this technique lies in the ability to direct tissue regeneration based on the stage of differentiation which the cells are in at the time of implantation. That is, with respect to cartilage, the state of the cells at implantation may control the ultimate tissue type formed.

As used herein the terms "chondroinductive agent" or "chondroinductive factor" refers to any natural or synthetic, organic or inorganic chemical or biochemical compound or combination or mixture of compounds, or any mechanical or other physical device, container, influence or force that can be applied to human mesenchymal stem cells which are in a three dimensional format so as to effect their in vitro chondrogenic induction or the production of chondrocytes. The chondroinductive agent is preferably selected, individually or in combination, from the group consisting of (i) a glucocorticoid such as dexamethasone; (ii) a member of the transforming growth factor-β superfamily such as a bone morphogenic protein (preferably BMP-2 or BMP-4), TGF-β1, inhibin A or chondrogenic stimulating activity factor (CSA); (iii) a component of the collagenous extracellular matrix such as collagen I (particularly in the form of a gel); and (iv) a vitamin A analog such as retinoic acid.

As used herein the term "chemically defined medium" refers to a maintenance, growth or culture medium in which the composition of the invention can undergo in vitro chondrogenesis, particularly in accordance with the methods of the invention, and includes a minimum essential medium, ascorbate or an analog thereof, an iron source and insulin or an insulin-like growth factor.

As used herein the term "minimum essential medium" refers to any serum-free animal cell culture preparation or medium of known composition which will support the viability of human mesenchymal stem cells in vitro. Examples are any of the Eagle's based media, i.e., Dulbecco's Modified Eagle's Medium (DMEM); Iscove's Modified Eagle's Medium, alpha Modified Eagle's Medium, and also McCoy's 5A and BGJ$_b$ (Fitton-Jackson Modification).

As used herein the term "iron source" refers to any species that will release the reduced, ferric, form of iron to the medium, including but not limited to transferrin, $FeSO_4$ or ferritin.

As used herein the term "insulin" refers to any of the various insulins that are known. Insulins are divided into three categories according to promptness, duration and intensity of action following subcutaneous administration, i.e., as mentioned above, rapid, intermediate or long-acting. Crystalline regular insulin is prepared by precipitation in the presence of zinc chloride and modified forms have been developed to alter the pattern of activity. Protamine zinc insulin (PZI) is the result of the reaction of insulin and zinc with the basic protein, protamine, to form a protein complex which dissolves and is absorbed more slowly than crystalline regular insulin but is highly reliable for absorption at a steady rate. Isophane is a modified crystalline protamine zinc insulin whose effects are comparable to a mixture of predominantly regular insulin with a lesser portion of protamine zinc insulin. The extended and prompt insulin-zinc suspensions are also contemplated for use in the invention. The insulin can be, for example, of human bovine, ovine or other animal origin or can be a recombinant product.

Human insulin is now widely available as a result of its production by recombinant DNA techniques; in theory it should be slightly less immunogenic than purified porcine insulin, which in turn should be less immunogenic than bovine insulin. Bovine insulin differs from human insulin by three amino acid residues, whereas porcine differs from human insulin by only one amino acid at the carboxyl-terminus of the β-chain. However, when highly purified, all three insulins have a relatively low, but measurable, capacity to stimulate the immune response.

Short- or rapid-acting insulins are simply solutions of regular, crystalline zinc insulin (insulin injection) dissolved in a buffer at neutral pH. These have the most rapid onset of action but the shortest duration, i.e., glucose levels reach a low point within 20–30 minutes and return to baseline in about 2–3 hours.

Intermediate-acting insulins are formulated so that they dissolve more gradually when administered subcutaneously; their durations of action are thus longer. The two preparations most frequently used are neutral protamine Hagedorn (NPH) insulin (isophane insulin suspension) and Lente insulin (insulin zinc suspension). NPH insulin is a suspension of insulin in a complex with zinc and protamine in a phosphate buffer. Lente insulin is a mixture of crystallized (Ultralente) and amorphous (Semilente) insulins in an acetate buffer, which minimizes the solubility of insulin. The preparations have similar pharmacokinetic profiles.

Ultralente insulin (extended insulin zinc suspension) and protamine zinc insulin suspension are long-acting insulins; they have a very slow onset and a prolonged ("flat") peak of action. These insulins are advocated to provide a low basal concentration of insulin throughout the day.

As used herein the term insulin is also contemplated to encompass insulin analogs. Recent development of insulin that have altered rates of absorption have raised interest. Insulin with aspartate and glutamate substituted at positions B9 and B27, respectively, crystallizes poorly and has been termed "monomeric insulin". This insulin is absorbed more rapidly from subcutaneous depots and thus may be useful in meeting postprandial demands. By contrast, other insulin analogs tend to crystallize at the site of injection and are absorbed more slowly. Insulins with enhanced potency have been produced by substitution of aspartate for histidine at position B10 and by modification of the carboxyl-terminal residues of the B chain.

Isolation, Purification and Culture Expansion of Human Mesenchymal Stem Cells

The human mesenchymal stem cells isolated and purified as described here can be derived, for example, from bone marrow, blood, dermis or periosteum. When obtained from bone marrow this can be marrow from a number of different sources, including plugs of femoral head cancellous bone pieces, obtained from patients with degenerative joint disease during hip or knee replacement surgery, or from aspirated marrow obtained from normal donors and oncology patients who have marrow harvested for future bone marrow transplantation. The harvested marrow is then prepared for cell culture. The isolation process involves the use of a specially prepared medium that contains agents which allow for not only mesenchymal stem cell growth without differentiation, but also for the direct adherence of only the mesenchymal stem cells to the plastic or glass surface of the culture vessel. By creating a medium which allows for the selective attachment of the desired mesenchymal stem cells which were present in the mesenchymal tissue samples in very minute amounts, it then became possible to separate the mesenchymal stem cells from the other cells (i.e. red and white blood cells, other differentiated mesenchymal cells, etc.) present in the mesenchymal tissue of origin.

Bone marrow is the soft tissue occupying the medullary cavities of long bones, some haversian canals, and spaces between trabeculae of cancellous or spongy bone. Bone marrow is of two types: red, which is found in all bones in early life and in restricted locations in adulthood (i.e. in the spongy bone) and is concerned with the production of blood cells (i.e. hematopoiesis) and hemoglobin (thus, the red color); and yellow, which consists largely of fat cells (thus, the yellow color) and connective tissue.

As a whole, bone marrow is a complex tissue comprised of hematopoietic cells, including the hematopoietic stem cells, and red and white blood cells and their precursors; and a group of cells including mesenchymal stem cells, fibroblasts, reticulocytes, adipocytes, and endothelial cells which contribute to the connective tissue network called "stroma". Cells from the stroma regulate the differentiation of hematopoietic cells through direct interaction via cell surface proteins and the secretion of growth factors and are involved in the foundation and support of the bone structure. Studies using animal models have suggested that bone marrow contains "pre-stromal" cells which have the capacity to differentiate into cartilage, bone, and other connective tissue cells. (Beresford, J. N.: Osteogenic Stem Cells and the Stromal System of Bone and Marrow, *Clin. Orthop.*, 240:270, 1989). Recent evidence indicates that these cells, called pluripotent stromal stem cells or mesenchymal stem cells, have the ability to generate into several different types of cell lines (i.e. osteocytes, chondrocytes, adipocytes, etc.) upon activation, depending upon the influence of a number of bioactive factors. However, the mesenchymal stem cells are present in the tissue in very minute amounts with a wide variety of other cells (i.e. erythrocytes, platelets, neutrophils, lymphocytes, monocytes, eosinophils, basophils, adipocytes, etc.).

As a result, a process has been developed for isolating and purifying human mesenchymal stem cells from tissue prior to differentiation and then culture expanding the mesenchymal stem cells to produce a valuable tool for musculoskeletal therapy. The objective of such manipulation is to greatly increase the number of mesenchymal stem cells and to utilize these cells to redirect and/or reinforce the body's normal reparative capacity. The mesenchymal stem cells are expanded to great numbers and applied to areas of connective tissue damage to enhance or stimulate in vivo growth for regeneration and/or repair, to improve implant adhesion to various prosthetic devices through subsequent activation and differentiation, or enhance hemopoietic cell production, etc.

Several media have been prepared which are particularly well suited to the desired selective attachment and are referred to herein as "Complete Media" when supplemented with serum as described below. One such medium is an augmented version of Dulbecco's Modified Eagle's Medium-Low Glucose (DMEM-LG), which is well known and readily commercially available.

The commercial formulation is supplemented with 3700 mg/l of sodium bicarbonate and 10 ml/l of 100× antibiotic-antimycotic containing 10,000 units of penicillin (base), 10,000 $\mu$g of streptomycin (base) and 25 $\mu$g of amphotericin B/ml utilizing penicillin G (sodium salt), streptomycin sulfate, and amphotericin B as FUNGIZONE® in 0.85% saline.

The medium described above is made up and stored in 90 ml per 100 ml or 450 ml per 500 ml bottles at 4° C. until ready to use. For use, 10 ml or 50 ml of fetal bovine serum (from selected lots) is added to the bottles of media to give a final volume of 10% serum. The medium is warmed to 37° C. prior to use.

In this regard, it was also found that $BGJ_b$ medium (Gibco, Grand Island, N.Y.) with tested and selected lots of 10% fetal bovine serum (J. R. Scientific, Woodland, Calif., or other suppliers) was well suited for use in the invention. This medium, which was also a "Complete Medium", contained factors which also stimulated mesenchymal stem cell growth without differentiation and allowed for the selective attachment through specific protein binding sites, etc. of only the mesenchymal stem cells to the plastic surfaces of Petri dishes.

In addition, it was also found that the medium F-12 Nutrient Mixture (Ham) (Gibco, Grand Island, N.Y.) exhibited the desired properties for selective mesenchymal stem cell separation.

As indicated above, the complete medium can be utilized in a number of different isolation processes depending upon the specific type of initial harvesting processes used in order to prepare the harvested bone marrow for cell culture separation. In this regard, when plugs of cancellous bone marrow were utilized, the marrow was added to the complete medium and vortexed to form a dispersion which was then centrifuged to separate the marrow cells from bone pieces, etc. The marrow cells (consisting predominantly of red and white blood cells, and a very minute amount of mesenchymal stem cells, etc.) were then dissociated into single cells by sequentially passing the complete medium containing the marrow cells through syringes fitted with a series of 16, 18, and 20 gauge needles. It is believed that the advantage produced through the utilization of the mechanical separation process, as opposed to any enzymatic separation process, was that the mechanical process produced little cellular change while an enzymatic process could produce cellular damage particularly to the protein binding sites needed for culture adherence and selective separation, and/or to the protein sites needed for the production of monoclonal antibodies specific for said mesenchymal stem cells. The single cell suspension (which was made up of approximately $50-100 \times 10^6$ nucleated cells) was then subsequently plated in 100 mm dishes for the purpose of selectively separating and/or isolating the mesenchymal stem cells from the remaining cells found in the suspension.

When aspirated marrow was utilized as the source of the human mesenchymal stem cells, the marrow stem cells (which contained little or no bone chips but a great deal of blood) were added to the complete medium and fractionated with Percoll (Sigma, St. Louis, Mo.) gradients. The Percoll gradients separated a large percentage of the red blood cells and the mononucleate hematopoietic cells from the low density platelet fraction which contained the marrow-derived mesenchymal stem cells. In this regard, the platelet fraction, which contained approximately $30-50 \times 10^6$ cells was made up of an undetermined amount of platelets, $30-50 \times 10^6$ nucleated cells, and only about 50–500 mesenchymal stem cells depending upon the age of the marrow donor. The low density platelet fraction was then plated in the Petri dish for selective separation based upon cell adherence.

In this regard, the marrow cells obtained from either the cancellous bone or iliac aspirate (i.e. the primary cultures) were grown in complete medium and allowed to adhere to the surface of the Petri dishes for one to seven days according to the conditions set forth in Example 1 below. Since minimal cell attachment was observed after the third day, three days was chosen as the standard length of time at which the non-adherent cells were removed from the cultures by replacing the original complete medium with fresh complete medium. Subsequent medium changes were performed every four days until the culture dishes became confluent which normally required 14–21 days. This represented a $10^3-10^4$ fold increase in the number of undifferentiated human mesenchymal stem cells.

The cells were then detached from the culture dishes utilizing a releasing agent such as trypsin with EDTA (ethylene diaminetetra-acetic acid) (0.25% trypsin, 1 mM EDTA (1X), Gibco, Grand Island, N.Y.). The releasing agent was then inactivated and the detached cultured undifferentiated mesenchymal stem cells were washed with complete medium for subsequent use.

Isolation of Non-Cultured Human Mesenchymal Stem Cells

It is also possible to use an isolated, non-cultured non-homogeneous human mesenchymal stem cell preparation in the composition and methods of the invention. MSCs can be isolated as non-cultured, non-homogeneous preparations, such as by density gradient fractionation, from tissue such as bone marrow, blood (including peripheral blood), periosteum and dermis, and other tissues which have mesodermal origins. In this regard, it has been found that although these mesenchymal stem cells are normally present in bone marrow, for example, in very minute amounts and that these amounts greatly decrease with age (i.e. from about $\frac{1}{10,000}$ cells in a relatively young patient to as few as $\frac{1}{2,000,000}$ in an elderly patient), human mesenchymal stem cell preparations can be isolated from tissue, particularly bone marrow, so as to be substantially free of other types of cells in the marrow. It is contemplated that the isolated fractionation preparation will comprise cells of which at least about 90%, and preferably at least about 95%, are human mesenchymal stem cells.

Marrow in femoral head cancellous bone pieces is obtained from patients with degenerative joint disease during hip or knee joint replacement surgery. In addition, marrow is also obtained by iliac aspirate from normal donors and oncology patients who are having marrow harvested for future bone marrow transplantation. All of the oncology patients have malignancies unrelated to the stromal cells and their stromal cells express normal karyotype.

The bone marrow is aspirated from several sites from the sternum, rib and iliac crest under sterile working conditions. Aspiration is slow to avoid clotting in the syringe. Multiple aspiration sites from the bone with one or two skin penetration sites provides high nucleated cell counts contaminated with relatively low volume of diluting peripheral blood. The syringe is equipped with a conventional sternal aspiration needle, 12 gauge bone marrow aspiration trocar needle or trephine needle used for bone marrow harvesting. Twenty-five ml. of bone marrow is harvested into heparinized syringes 91000 units/liter of sterile saline).

The human bone marrow is then transferred to a 50 ml. centrifuge tube and centrifuged at low speed to yield a cell pellet. Fat and plasma are removed from the centrifuge tube by aspiration. The cell pellet is resuspended in a sterile solution containing 20 mM Tris base and 0.7% ammonium chloride. The pH is adjusted to 7.2 and the suspension is then centrifuged at low speed to yield a cell pellet. The Tris NH$_4$Cl solution is aspirated from the cell pellet and the pellet is resuspended in 10 ml of DMEM medium. The resuspended pellet is carefully layered onto a 50 ml tube containing 35 ml. of 70% Percoll™. The tube is centrifuged at 460×g for 15 minutes. The upper 25% of the gradient or 12.5 ml of the Percoll gradient containing mesenchymal stem cells, platelets and other cells is harvested with a pipet. This fraction is transferred to a 50 ml centrifuge tube to which 25 ml of medium has been added. The tube is inverted several times to suspend the cells and then recentrifuged at low speed to yield a cell pellet. This process is repeated twice with fresh medium.

The human bone marrow sample is then concentrated to remove plasma and cleared of red blood cells either by NH$_4$Cl treatment as described above or by passage of the samples over a Leukosorb™ filter contained in a syringe cartridge filter removing fat, red blood cells and plasma. The cell fraction retained by the filter is eluted from the filter using a buffer containing sodium citrate. The MSC enriched cells which elute from the filter are then further enriched by passage over an hydroxyapatite column which preferentially binds MSCs. The syringe filter eluate containing red blood cell depleted bone marrow is passed over a syringe filled with hydroxyapatite. The hydroxyapatite used in this example is obtained from Interpore Corp. (IP200). Porous hydroxyapatite granules having a minimum pore size of 200 micrometers and a maximum pore size of up to 500 micrometers are used. The cells are loaded into the syringe containing hydroxyapatite in a sterile transfer step. The cells are allowed to bind for 15 minutes and buffer present in the cells allowed to flow through. The syringe is then washed one time with 15 ml. of medium (DMEM). The base of the syringe which is threaded is unscrewed and the implant material pushed out of the syringe with the plunger for further processing or for direct intraoperative application to a graft site.

A monoclonal antibody separation is then performed as follows. Dynabeads M-450 (Dynal (r) Inc. Lake Success, N.Y.) are coupled to anti-MSC monoclonal antibodies having ATCC Accession Number HB 10743, HB 10744 and HB 10745 by incubating antibody with secondary antibody coated Dynabeads (2.0 µg anti-MSC antibody/mg Dynabead) in PBS for 30 minutes at 4° C. A bead solution contain $1 \times 10^7$ Dynabeads/ml. is used. Antibody is incubated. The Dynabeads are collected by placing the solution containing beads and antibodies into a Magnetic Particle Concentrator (Dynal MPC). The supernatant is removed while the Dynabeads are kept on the wall of the test tube with the magnet. Dynabeads are cleared of free antibody by washing 5 times with PBS. After the last wash, the Dynabeads are collected and the supernatant is removed. To the 80 ml. of Dynabeads is added 35 ml. of heparinized bone marrow. The cells are incubated with the Dynabeads for 15 minutes with shaking. The Dynabeads with attached MSCs are then collected using the Dynal MPC. The supernatant is removed and the magnetic particles washed concentration with PBS. Approximately $200 \times 10^6$ cells are collected on the Dynabeads. The cells are detached from the beads by incubating beads in 50 ml. of a solution containing 1% EDTA. The EDTA solution is removed from the cells by centrifugation at low speed and results in a cell pellet suitable for use in the invention.

EXAMPLE 1

In Vitro Chondrogenesis using Dexamethasone

In our preliminary studies we have found that rabbit bone marrow-derived mesenchymal progenitor cells, cultured for 14 days and then seeded into either ceramic cubes or collagen sponges and implanted subcutaneously into nude mice will produce bone and cartilage within 3 weeks (FIG. 1).

The present invention contemplates that the creation of a precartilage condensation in vitro promotes chondrogenesis in mesenchymal progenitor cells derived from postnatal bone marrow, where such populations contain either stem or progenitor cells for chondrocytes. This was accomplished using the pellet culture system, which was developed for use with isolated growth plate cells (Kato et al., *PNAS*, 85:9552–9556, 1988; Ballock and Reddi, *J Cell Biol*, 126:1311–1318, 1994) and has also been used to maintain expression of the cartilage phenotype of chondrocytes placed in culture (Solursh, *J Cell Biochem*, 45:258–260, 1991).

Both rabbit and human bone marrow-derived cells were used. Bone marrow-derived mesenchymal progenitor cells were harvested from New Zealand white rabbit tibia or iliac crest by aspiration into a syringe containing 3000 U heparin. These cells were plated at 20 million/100 mm dish in DMEM containing 10% foetal bovine serum and grown for 14 days at 37° C. in 5% $CO_2$, with medium changes every four days. A serum screen was first done to identify lots of serum that support the proliferation of these cells and produce the most bone and cartilage of first passage cells in the in vivo ceramic cube assay referenced above. After colonies of adherent cells were formed on the culture dishes (approximately 10–14 days), the cells were trypsinized off the dishes and counted. Aliquots of 200,000 cells were centrifuged at 500×g for 10 minutes in sterile 15 ml conical polypropylene tubes in DMEM with 10% serum, 50 ng/ml ascorbate-2-phosphate $+/-10^{-7}M$ dexamethasone (DEX) and then incubated at 37° C. in a 5% $CO_2$ incubator for up to 3 weeks. After 24 hours some portion of the cells had formed pellets in the tubes, with some cells remaining in a monolayer on the sides of the tube. After 3 weeks many of the pellets had fallen apart. Of the pellets that remained, none contained cells with the appearance of chondrocytes and no type II collagen staining was found. As an alternative to serum, a defined medium supplement (ITS+Premix™, Collaborative Biomedical Products) was tried. This supplement has previously been used for pellet culture of growth plate chondrocytes (Ballock and Reddi, *J Cell Biol*, 126:1311–1318, 1994). The supplement consists of DMEM with insulin (6.25 µg/ml), transferrin (6.25 µg/ml), selenious acid (6.25 µg/ml), linoleic acid (1.25 µg/ml) and bovine serum albumin (5.35 µg/ml), (concentrations given are final). To this was added pyruvate (1 mM), ascorbate-2 phosphate (50 µg/ml), with or without $10^{-7}M$ dexamethasone (DEX). For some experiments the 10% FBS containing medium was not replaced. The spun cells were incubated at 37° C. in 5% $CO_2$. Human marrow cells were obtained from healthy donors by aspiration of the iliac crest. The culture conditions were identical to those used for the rabbit cells. Within 24 hours of incubation, the cells formed a pellet. Medium changes were carried out every 2 days. When pellets were harvested at time points to 21 days, the alkaline phosphatase activity of each pellet was determined by incubation with p-nitrophenyl phosphate and determination of the absorbance at 405 nm. The absorbance values obtained in a typical experiment for pellets incubated +/−DEX increased three to five-fold during the first 14 days of culture and remained at the elevated level until day 21. For histological and immunohistochemical analyses, the pellets were frozen in OCT and 5 µm sections were cut. Toluidine blue staining and immunohistochemistry were done, the latter with antibodies to extracellular matrix components (FIGS. 2 and 3) including: anti-collagen types I, II and X, and anti-glycosaminoglycan antibodies 3-B-3, 7-D-4 (chondroitin sulfate), and 5-D-4 (keratan sulfate). Reactivity was detected with either FITC-linked secondary antibodies and fluorescence microscopy or alkaline phosphatase-linked antibodies and substrate. Pellets were also extracted in 4M guanidine, 20 mM sodium acetate containing protease inhibitors and subjected to immunolocalization after separation by SDS-PAGE and Western blotting.

By day 7 of culture some metachromatic staining of parts of the +DEX defined medium pellets could be seen with toluidine blue. By day 14, the +DEX pellets contained obvious metachromatic staining around a region of internally located cells, which had the appearance of hypertrophic chondrocytes. Those cells on the periphery of the pellets remained flat and did not show metachromasia. By day 21, the +DEX pellets resembled a ball of hypertrophic chondrocytes. In contrast, the −DEX defined medium pellets all shrunk in size and in many cases fell apart by 21 days in culture. No obvious hypertrophic cells were evident in any −DEX pellet.

Immunohistochemistry using antibody to type II collagen was positive in the +DEX defined medium pellets as early as 7 days in some samples (FIG. 3A). By day 14, the matrix of the region of hypertrophic-like cells stained positively for type II collagen (FIG. 3B). In some experiments, the entire pellet stained positively for type II collagen when analyzed at day 21 (FIG. 3C). In others, a thin outer region was still negative for type II collagen. Positive staining for type X collagen was also seen by day 14 (FIG. 3D). The matrix of the hypertrophic cells also stained positively for chondroitin sulfate (7-D-4 in FIG. 3E; 3-B-3(+) in FIG. 3F) and keratan sulfate (5-D-4 in FIG. 3G)., with some differences in staining distribution. None of the pellets grown in the absence of DEX had positive staining for type II collagen. Immunostaining of the SDS-PAGE separated, Western blotted pellet extracts with anti-type II antibody gave a positive band with the migration of $\alpha$ (II) chains (FIG. 4). In subsequent experiments, we found that this same defined medium, +DEX, did not produce chondrogenesis in either monolayer or micromass cultures. These observations are important and indicate that early cell-cell interactions are required for chondrogenesis. Thus, through a combination of creating an in vitro cell condensation and adding the appropriate permissive factors, we have been able to produce chondrogenesis in cells from a postnatal mammalian bone marrow source.

The above demonstrates a culture system in which rabbit and human bone marrow-derived mesenchymal progenitor cells differentiate into hypertrophic chondrocytes. The sequence of events resembles that of chondrogenesis in embryonic limb formation. Since all components are defined, the system can be used for studies of the effects of growth factors etc. on the progression of chondrogenesis. It is also applicable to studies of the molecular control of mammalian chondrogenesis from progenitor cells.

This system utilizes a postnatal source and adds to the data concerning bone marrow-derived progenitor cells. In vitro systems have been used by others to show that these cell populations have osteogenic and adipocytic potential; we demonstrate here that at least a sub-set of that population has chondrogenic potential. This system will facilitate the exploration of the control of chondrogenesis and may lead to an understanding of what factors are required to promote this process in vivo. This has clinical applicability for cartilage repair.

EXAMPLE 2

In Vitro Chondrogenesis using Dexamethasone and TGF-$\mu$1

Rabbit and human marrow-derived mesenchymal cells were obtained and pelleted as described in Example 1. The culture media were modified as follows.

Rabbit marrow-derived mesenchymal cells were cultured as described in Example 1, with either (i) the addition of TGF-$\beta$1 (10 ng/ml) or (ii) the addition of TGF-$\beta$1 (10 ng/ml) and the deletion of dexamethasone. Human marrow-derived mesenchymal cells were cultured as described in Example 1, with either (i) the addition of TGF-$\beta$1 (10 ng/ml) or (ii) the addition of TGF-$\beta$1 (10 ng/ml) and the deletion of dexamethasone.

In the rabbit cell cultures, differentiation of the MSCs into chondrocytes was observed in the presence of TGF-$\beta$1, both with and without dexamethasone. In the human cell cultures, differentiation of the MSCs into chondrocytes was observed in the presence of TGF-$\beta$1 with dexamethasone, but not in its absence.

EXAMPLE 3

In Vitro Chondrogenesis using Dexamethasone and BMP-2

Rat marrow-derived mesenchymal cells were obtained and pelleted as described in Example 1. The culture media were modified as follows. Rat marrow-derived mesenchymal cells were cultured as described in Example 1, with the addition of BMP-2 at 10 ng/ml and 100 ng/ml in the presence or absence of dexamethasone ($10^{-7}$M). Differentiation of the MSCs into chondrocytes was observed in the presence of BMP-2 with dexamethasone, but not in its absence.

What is claimed is:

1. A composition for the in vitro chondrogenesis of human mesenchymal precursor cells and the in vitro formation of human chondrocytes therefrom, which composition comprises isolated human mesenchymal stem cells condensed into close proximity as a packed cell pellet and at least one chondroinductive agent in contact therewith.

2. The composition of claim 1 wherein the mesenchymal stem cells are isolated, culture expanded human mesenchymal stem cells.

3. The composition of claim 1 wherein the mesenchymal stem cells are in a chemically defined serum-free environment.

4. The composition of claim 1 wherein the chondroinductive agent is selected from the group consisting of (i) a glucocorticoid; (ii) a member of the transforming growth factor-$\beta$ superfamily; and (iii) a component of the collagenous extracellular matrix.

5. The composition of claim 4 wherein the glucocorticoid is dexamethasone.

6. The composition of claim 4 wherein the member of the transforming growth factor superfamily is selected from the group consisting of a bone morphogenic protein, TGF-$\beta$ 1, inhibin A and chondrogenic stimulating activity factor.

7. The composition of claim 6 wherein the bone morphogenic protein is BMP-4.

8. The composition of claim 4 wherein the component of the collagenous extracellular matrix is collagen I.

9. The composition of claim 8 wherein the collagen I is in the form of a gel.

10. The composition of claim 1 wherein the chondroinductive agent is a combination of dexamethasone and TGF-$\beta$1.

11. A process for producing chondrocytes from mesenchyrnal stem cells by contacting mesenchymal stem cells with a chondroinductive agent in vitro wherein the stem cells are condensed into close proximity as a packed cell pellet.

12. The process of claim 11 wherein the mesenchymal stem cells are isolated, culture expanded human mesenchymal stem cells.

13. The process of claim 11 wherein the mesenchymal stem cells are in a chemically defined serum-free environment.

14. The process of claim 11 wherein the chondroinductive agent is selected from the group consisting of (i) a glucocorticoid; (ii) a member of the transforming growth factor-$\beta$ superfamily; and (iii) a component of the collagenous extracellular matrix.

15. The process of claim 11 wherein the chondroinductive agent is a combination of dexamethasone and TGF-$\beta$1.

16. The process of claim 11 wherein the step of contacting comprises culturing a pellet of human mesenchymal stem cells in a chemically defined serum-free medium.

17. The process of claim 16 wherein the chemically defined serum-free medium comprises (1) a chemically defined minimum essential medium; (2) ascorbate or an analog thereof; (3) an iron source; (4) insulin or an insulin-like growth factor; and (5) at least one chondroinductive agent or factor.

18. The method of claim 11 wherein the cells are cultured with the chondroinductive composition and thereafter placed in a rigid porous vessel.

19. The method of claim 18 wherein the rigid porous vessel is a ceramic cube.

20. A process for inducing chondrogenesis in mesenchymal stem cells by contacting mesenchymal stem cells with a chondroinductive agent in vitro wherein the stem cells are condensed into close proximity as a packed cell pellet.

21. The process of claim 20 wherein the mesenchymal stem cells are isolated, culture expanded human mesenchymal stem cells.

22. The process of claim 20 wherein the mesenchymal stem cells are in a chemically defined serum-free environment.

23. The process of claim 20 wherein the chondroinductive agent is selected from the group consisting of (i) a glucocorticoid; (ii) a member of the transforming growth factor-β superfamily; and (iii) a component of the collagenous extracellular matrix.

24. The process of claim 20 wherein the chondroinductive agent is a combination of dexamethasone and TGF-β1.

25. The process of claim 20 wherein the step of contacting comprises culturing a pellet of human mesenchymal stem cells in a chemically defined serum-free medium.

26. The process of claim 25 wherein the chemically defined serum-free medium comprises (1) a chemically defined minimum essential medium; (2) ascorbate or an analog thereof; (3) an iron source; (4) insulin or an insulin-like growth factor; and (5) at least one chondroinductive agent or factor.

27. The method of claim 20 wherein the cells are cultured with the chondroinductive composition and thereafter placed in a rigid porous vessel.

28. The method of claim 27 wherein the rigid porous vessel is a ceramic cube.

* * * * *

UNITED STATES PATENT AND TRADEMARK OFFICE
CERTIFICATE OF CORRECTION

PATENT NO. : 5,908,784
DATED : June 1, 1999
INVENTOR(S) : Johnstone et al.

It is certified that error appears in the above-identified patent and that said Letters Patent is hereby corrected as shown below:

Column 11, Line 49, replace "TGF-µ1" with --TGF-β1--.

Column 12, Lines 47-48, replace "mesenchyrnal" with --mesenchymal--.

Column 12, Line 49, replace "stern" with --stem--.

Signed and Sealed this

Twenty-first Day of December, 1999

Attest:

Q. TODD DICKINSON

*Attesting Officer*    Acting Commissioner of Patents and Trademarks